(12) United States Patent
Raible (10) Patent No.: US 12,209,983 B2
(45) Date of Patent: Jan. 28, 2025

(54) SENSOR OPERABLE TO MEASURE OZONE CONCENTRATION AND A METHOD FOR USING A SENSOR

(71) Applicant: Sciosense B.V., AE Eindhoven (NL)

(72) Inventor: Stefan Raible, Tübingen (DE)

(73) Assignee: Sciosense B.V., AE Eindhoven (NL)

( * ) Notice: Subject to any disclaimer, the term of this patent is extended or adjusted under 35 U.S.C. 154(b) by 456 days.

(21) Appl. No.: 17/299,402

(22) PCT Filed: Nov. 28, 2019

(86) PCT No.: PCT/EP2019/082908

§ 371 (c)(1),
(2) Date: Jun. 3, 2021

(87) PCT Pub. No.: WO2020/126393

PCT Pub. Date: Jun. 25, 2020

(65) Prior Publication Data

US 2022/0050072 A1 Feb. 17, 2022

(30) Foreign Application Priority Data

Dec. 21, 2018 (EP) ..................................... 18215454

(51) Int. Cl.
*G01N 27/12* (2006.01)
*G01N 1/38* (2006.01)
(Continued)

(52) U.S. Cl.
CPC .............. *G01N 27/125* (2013.01); *G01N 1/38* (2013.01); *G01N 1/44* (2013.01); *G01N 33/0039* (2013.01)

(58) Field of Classification Search
CPC .......... G01N 27/125; G01N 1/38; G01N 1/44; G01N 33/0039; G01N 27/12
See application file for complete search history.

(56) References Cited

U.S. PATENT DOCUMENTS 6,054,098 A 4/2000 Kato et al.
8,480,862 B2 7/2013 Berkman et al.
(Continued)

FOREIGN PATENT DOCUMENTS

CN 101243369 A 8/2008
CN 201765180 U 3/2011
(Continued)

OTHER PUBLICATIONS

Williams, D. et al., "Validation of low-cost ozone measurement instruments suitable for use in an air-quality monitoring network" Measurement Science and Technology, May 3, 2013, 12 pages.
(Continued)

*Primary Examiner* — Xin Y Zhong
(74) *Attorney, Agent, or Firm* — Slater Matsil, LLP (57) ABSTRACT

In an embodiment a sensor includes an outer housing, an inner housing disposed within an interior of the outer housing or connected to the interior of the outer housing, an ozone sensing component disposed within an interior of the inner housing, an ozone modifying component disposed within the interior of the outer housing, a substrate on which the ozone sensing component and the ozone modifying component are disposed, a first inlet integrated into the outer housing, the first inlet being configured to conduct ambient gaseous matter from an outside of the outer housing into the interior of the outer housing and a second inlet integrated into the inner housing, the second inlet being configured to conduct the gaseous matter from the interior of the outer housing into the interior of the inner housing and adjacent to the ozone sensing component, wherein the ozone sensing component is configured to generate a sensing component signal corresponding to an ozone concentration of the gaseous matter within the interior of the inner housing, and wherein the ozone modifying component is configured to alter the ozone concentration of the gaseous matter within the interior of the outer housing.

13 Claims, 6 Drawing Sheets

(51) Int. Cl.
*G01N 1/44* (2006.01)
*G01N 33/00* (2006.01)

(56) References Cited

U.S. PATENT DOCUMENTS

| | | | |
|---|---|---|---|
| 10,309,915 | B2 | 6/2019 | Tremblay |
| 2003/0221976 | A1 | 12/2003 | Friedel et al. |
| 2016/0349201 | A1* | 12/2016 | Graunke ............ G01N 33/0016 |
| 2017/0122921 | A1 | 5/2017 | Henshaw et al. |
| 2017/0219479 | A1* | 8/2017 | Bilenko ................. G01N 21/11 |
| 2019/0212287 | A1* | 7/2019 | Raible ................ G01N 33/0039 |
| 2019/0265183 | A1* | 8/2019 | Brown ................. G01N 27/125 |

FOREIGN PATENT DOCUMENTS

| | | |
|---|---|---|
| CN | 106133518 A | 11/2016 |
| CN | 107430081 A | 12/2017 |
| CN | 207596464 U | 7/2018 |
| EP | 0767905 A1 | 4/1997 |
| FR | 2971845 A1 | 8/2012 |
| JP | H04191648 A | 7/1992 |
| JP | 2003329585 A | 11/2003 |
| KR | 20090086766 A | 8/2009 |
| TW | 201510520 A | 3/2015 |
| WO | 2017202571 A1 | 11/2017 |

OTHER PUBLICATIONS

Bolb Inc., "UV-C LED Product Specifications 6060 SMD Packaged Led," V1/1, Apr. 2018, 11 pages.

Central Semiconductor Corp., "Package Details—TO-39, Mechanical Drawing," Jul. 16, 2018, 2 pages.

David E. Williams et al, "Validation of low-cost ozone measurement instruments suitable for use in an air-quality monitoring network," Measurement Science And Technology, IOP, Publishing, vol. 24, May 3, 2013, 12 pages.

Harvard University, "Chapter 10, Stratospheric Ozone," http://acmg.seas.harvard.edu/people/faculty/dj/book/bookchap10.html; retrieved from the Internet on Jul. 19, 2018, 21 pages.

\* cited by examiner

FIG 5C

SENSOR OPERABLE TO MEASURE OZONE CONCENTRATION AND A METHOD FOR USING A SENSOR

This patent application is a national phase filing under section 371 of PCT/EP2019/082908, filed Nov. 28, 2019, which claims the priority of European patent application 18215454.2, filed Dec. 21, 2018, each of which is incorporated herein by reference in its entirety.

TECHNICAL FIELD

The present disclosure is related to a sensor operable to measure ozone concentration, an apparatus wherein a sensor is integrated in the apparatus and a method for using a sensor.

BACKGROUND

A sensor operable to measure ozone concentration is a gas sensor used to detect the presence of ozone, written as O3. Ozone is an oxidant and has several industrial and consumer applications related to oxidation. The oxidizing potential of ozone, however, may cause ozone to damage mucous and respiratory tissues in animals and also to damage tissues in plants. Gas-sensing components typically have sensitivities not only for one gas but for several gases. Thus, for the detection of a specific gas such as ozone, a gas sensor has to be realized such that a sufficient selectivity and sensitivity for the to-be-measured gas can be achieved.

SUMMARY

Embodiments provide a sensor operable to measure ozone concentration, an apparatus wherein a sensor is integrated in the apparatus and a method for using a sensor that improves the selectivity of a sensing component.

In an embodiment, a sensor is operable to measure ozone concentration. The sensor comprises an inner housing disposed within an interior of an outer housing or connected to the interior of the outer housing; an ozone sensing component disposed within an interior of the inner housing; an ozone modifying component disposed within the interior of the outer housing; a substrate on which the ozone sensing component and the ozone modifying component are disposed; a first inlet integrated into the outer housing, the first inlet being configured to conduct ambient gaseous matter from an outside of the outer housing into the interior of the outer housing; and a second inlet integrated into the inner housing. The second inlet is configured to conduct the gaseous matter from the interior of the outer housing into the interior of the inner housing and adjacent to the ozone sensing component.

Furthermore, the ozone sensing component is operable to generate a sensing component signal corresponding to the ozone concentration of the gaseous matter within the interior of the inner housing. The ozone modifying component is operable to alter the ozone concentration of the gaseous matter within the interior of the outer housing.

The sensor comprises the outer housing.

Advantageously, the ozone modifying component is able to change an ozone concentration. Since an ozone concentration of the ambient gaseous matter and a changed ozone concentration can alternatively be provided to the ozone sensing component, an on-line calibration can be performed. Gaseous matter may be named air or gas. The outer housing separates the ambient air or gas from the ozone modifying component, abbreviated modifying component. The influence of particles, dust or light in the ambience and of mechanical forces etc. on the modifying component is reduced by the outer housing. Furthermore, the inner housing separates the interior of the outer housing from the ozone sensing component, abbreviated sensing component. Thus, an influence of the modifying component on the sensing component is reduced. The sensor operable to measure ozone concentration is realized as ozone sensor, abbreviated sensor.

In an embodiment, the sensing component comprises a metal oxide sensor element. The metal oxide sensor element comprises a sensing layer made out of a metal oxide semiconductor. Ozone can react with the surface of the metal oxide semiconductor and is able to change a resistivity of the sensing layer. Thus, the resistivity of the sensing layer is a function of the ozone concentration.

Advantageously, the sensing component measures a raw signal of ozone concentration in a first phase and a calibration signal of the ozone concentration in a second phase. The calibration signal is measured at a value of the ozone concentration that is set or predetermined by the modifying component. For example, the predetermined value of the ozone concentration may be zero.

In an embodiment, the sensing layer of the metal oxide sensor element comprises one of tungsten oxide and indium oxide. Advantageously, the metal oxide sensor element comprising tungsten oxide or indium oxide as sensing layer is able to detect ozone with a high sensitivity and selectivity.

The modifying component may be switched on and off by a control signal.

In an embodiment, the modifying component includes a heat source. The heat source is operable to decrease the ozone concentration of the gaseous matter within the interior of the outer housing. Advantageously, the ozone concentration decreases with rising temperature of the air or gas in the interior of the outer housing.

In an embodiment, the modifying component includes a light source. The light source may be operable to generate light comprising one or more wavelengths suitable for a photo-decomposition of ozone. The modifying component is operable to decrease the ozone concentration of the gaseous matter within the interior of the outer housing. The light source may e.g. be operable to generate light having a particular wavelength or range of wavelengths suitable for the photo-decomposition of ozone.

The light source may emit light with a wavelength between 190 nm and 370 nm, preferably between 240 nm and 320 nm.

Advantageously, the ozone concentration in the interior of the outer housing and, thus, also in the interior of the inner housing can be modulated in a reproducible manner. The light can be switched on and off with very short delay.

In an embodiment, an interior surface of the outer housing is substantially reflective to the one or more wavelengths. Light emitted by the light source can be reflected inside the outer housing. Thus, only a small amount of power for the modifying component is required to achieve a high light intensity inside the outer housing. The interior surface of the outer housing may be substantially reflective to the particular wavelength or range of wavelengths.

In an embodiment, the modifying component includes a plasma source. The plasma source is operable to decrease the ozone concentration of the gaseous matter within the interior of the outer housing.

In an embodiment, the modifying component includes an ozone source. The ozone source is operable to increase the ozone concentration of the gaseous matter within the interior of the outer housing. Advantageously, the ozone source generates a predetermined and stable value of ozone concentration in the interior of the outer hosing. Thus, the sensing component measures the raw signal in the first phase and the calibration signal in the second phase. The calibration signal is measured at a predetermined or set not-zero value of ozone concentration. The ozone source may be named ozonator. The ozone source may generate a reference ozone concentration.

In an embodiment, the ozone source includes a light source. The light source is operable to generate light comprising one wavelength or more wavelengths suitable for a photo-generation of ozone. The light source may comprise at least a light-emitting diode. The wavelengths may be shorter than the wavelengths described above. The wavelengths may be in the ultraviolet range. For example, the light source may emit light with a wavelength between 100 nm and 240 nm, preferably between 140 nm and 230 nm, e.g. at approximately 185 nm.

In an embodiment, the ozone source can perform a corona discharge. In the ozone source performing the corona discharge, a current flows from an electrode with a high potential into a neutral fluid e.g. air and ionizes the fluid so as to create a region of plasma around the electrode. The ions generated eventually pass charge to nearby areas of lower potential, or recombine to form neutral gas molecules. Free radicals and ions generated in a corona reaction can produce ozone.

Alternatively, the ozone source is realized as a UV ozone generator or vacuum-ultraviolet ozone generator. The ozone source comprises a light source that emits a narrow-band ultraviolet light which generates ozone.

In an embodiment, an interior surface of the outer housing is covered or made from a material of a group comprising an iron-nickel alloy, a noble metal, an epoxide and a polytetrafluoroethylene. The interior surface of the outer housing is inert with respect to ozone. Thus, the interior surface of the outer housing does not change or does not significantly change the ozone concentration inside the outer housing.

In an embodiment, the sensor further includes a processor communicatively coupled to the sensing component and the modifying component. A memory of the sensor may be communicatively coupled to the processor. The processor is configured to execute one or more times and in any order predetermined steps including: Generating a raw signal with the sensing component; recording the raw signal to the memory; activating the modifying component; generating a calibration signal with the sensing component; recording the calibration signal to the memory; and deactivating the modifying component.

Advantageously, the sensing component generates the raw signal in the first phase and the calibration signal in the second phase. The processor determines a sensor output signal as a function of the raw signal and the calibration signal. The phases are set by the control signal.

In an embodiment, the predetermined steps further include determining from the raw signal and the calibration signal or a plurality of raw signals and calibration signals, the ozone concentration of the ambient gaseous matter outside of the outer housing. The plurality of raw signals may be determined in consecutive first phases and the plurality of calibration signals may be determined in consecutive second phases.

In an embodiment, the modifying component is activated such that the gaseous matter within the inner housing contains a minimum ozone concentration, and the calibration signal or the plurality of calibration signals are generated subsequent to the minimum ozone concentration being reached, and the calibration signal or the average of the plurality of calibration signals is equal to a baseline-offset value.

In an embodiment, the predetermined step of determining the ozone concentration of the ambient gaseous matter outside of the outer housing includes modifying the raw signal with the baseline-offset value such that the modified raw signal is indicative of the ozone concentration of the ambient gaseous matter outside of the outer housing.

In an embodiment, the predetermined step of determining the ozone concentration of the ambient gaseous matter outside of the outer housing includes determining an offset slope value from the plurality of calibration signals and modifying the raw signal with the baseline-offset value and the offset slope such that the modified raw signal is indicative of the ozone concentration of the ambient gaseous matter outside of the outer housing.

In an embodiment, the baseline-offset value is augmented by data transmitted from an external reference source communicatively coupled to the sensor.

In an embodiment, the baseline-offset and offset slope value are augmented by data transmitted from an external.

In an embodiment, the processor is communicatively coupled to an external reference source, and the baseline-offset value is augmented by data transmitted from the external reference source.

In an embodiment, the processor is communicatively coupled to an external reference source, and the baseline-offset value and the offset slope are augmented by data transmitted from the external reference source.

In an embodiment, the modifying component acts as internal reference source. The sensor performs an in-application calibration. The sensor performs a baseline reset to a known baseline, e.g. by active ozone destruction. The sensor may perform a span reset to the known baseline, e.g. by active ozone destruction. The sensor may be triggered to perform calibration at fixed time or at a baseline at low ozone levels and/or when the sensor is connected to power. A span correction may be triggered when medium to high ozone levels are present and/or when the sensor is connected to mains or a charger. Thus, more electric power is available that can be used to operate the modifying component.

In an embodiment, the sensor further including hardware operable to extract power alternately from a mobile power source and a stationary power source.

In an embodiment, the predetermined steps further include determining the power source is the stationary power source, and executing any of the predetermined steps mentioned above.

In an embodiment, the predetermined steps further include determining the power source is the mobile power source, and executing the predetermined steps of generating the raw signal with the sensing component, and, optionally, recording the raw signal to the memory.

In an embodiment, the sensor is free of a pump, a ventilator and a valve. Thus, the sensor is realized without active mechanical elements. Advantageously, a power consumption of the sensor is kept low and the size can be kept small.

In an embodiment, the sensor is integrated in an apparatus. The apparatus is realized as one of a group comprising a wearable device, an indoor air monitor, an outdoor air monitor, an automotive air monitor, an industrial air or gas monitor, a mobile device and a device for control of an ozone disinfection apparatus.

In an embodiment, a method for using a sensor comprises the steps of: Generating a raw signal with an ozone sensing component; activating an ozone modifying component; generating a calibration signal with the ozone sensing component; and deactivating the ozone modifying component.

Advantageously, at least two signals are used to determine the ozone concentration. Thus, an accuracy of the ozone measurement is increased.

The method for using a sensor may be implemented e.g. by the sensor according to one of the embodiments defined above. The method is performed on-line.

In an embodiment, the method further includes the step of determining the ozone concentration of the ambient gaseous matter outside of the outer housing from a raw signal and a calibration signal. A sensor output signal corresponds to the ozone concentration of the ambient gaseous matter outside of the outer housing.

In an embodiment, the method further includes the step of determining the ozone concentration of the ambient gaseous matter outside of the outer housing from a plurality of raw signals and a plurality of calibration signals.

Thus, the sensor output signal is determined using a plurality of first phases and a plurality of second phases. The sensor output signal is calculated as a function of the raw signals determined in the plurality of first phases and of the calibration signals determined in the plurality of second phases.

In an embodiment, the sensor is integrated in a wearable device.

In an embodiment, a sensor is operable to measure ozone concentration. The sensor comprises: an ozone sensing component and an ozone modifying component disposed in series with respect to each other by a channel; and an inlet port disposed immediately adjacent to the ozone modifying component. The inlet port is configured to conduct ambient gaseous matter from outside of the sensor and into the ozone modifying component. The channel is configured to conduct the gaseous matter conducted into the ozone modifying component to the ozone sensing component. The ozone sensing component is operable to generate a sensing component signal corresponding to the ozone concentration of the gaseous matter conducted to it. The ozone modifying component is operable to alter the ozone concentration of the gaseous matter conducted into the ozone modifying component.

In an embodiment, an ozone sensor comprises an inner housing disposed within an outer housing or coupled to the outer housing; an ozone sensing component disposed within the inner housing; an ozone modifying component disposed within the outer housing; a first inlet integrated into the outer housing and conducting ambient gas from an outside of the outer housing into the outer housing; and a second inlet integrated into the inner housing and conducting the gas from an interior of the outer housing into an interior of the inner housing and to the ozone sensing component.

Optionally, the sensor may comprise a substrate on which the ozone sensing component or the ozone modifying component or both are directly or indirectly disposed.

Alternatively, the ozone sensing component and the ozone modifying component are disposed in or at the outer housing. The substrate may be omitted or may be attached to the outer housing.

Advantageously, there is only one path for flow or diffusion of gas or air from the ambience to the sensing component. The same path is used backwards namely for flow or diffusion of gas or air from the sensing component to the ambience. The air or gas flows or diffuses from the ambience via the first inlet, the interior of the outer housing, the second inlet and the interior of the inner housing to the sensing component. The modifying component is able to change ozone concentration in the interior of the outer housing.

BRIEF DESCRIPTION OF THE DRAWINGS

The following description of figures of embodiments may further illustrate and explain aspects of the sensor operable to measure ozone concentration, the apparatus wherein a sensor is integrated in the apparatus and the method for using the sensor. Devices and circuit parts with the same structure and/or the same effect appear with equivalent reference symbols. In so far as devices or circuit parts correspond to one another in terms of their function in different figures, the description thereof is not repeated for each of the following figures. In the drawings.

DETAILED DESCRIPTION OF ILLUSTRATIVE EMBODIMENTS

Figure 1:
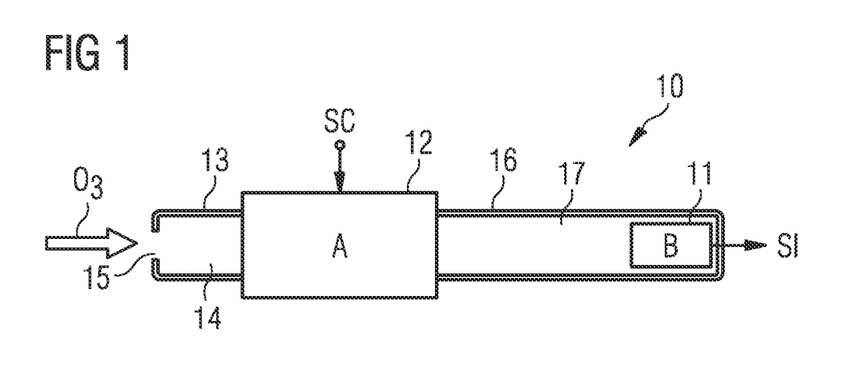
FIG. 1 shows an example of a sensor.

FIG. 1 shows an example of a sensor 10 that is implemented as an ozone sensor. The sensor 10 is operable to measure ozone concentration. The sensor 10 comprises an ozone sensing component 11, abbreviated as sensing component, and an ozone modifying component 12, abbreviated as modifying component. The modifying component 12 is configured to destroy ozone. The modifying component 12 may be named device. The modifying component 12 is realized such that it destroys ozone via a physical effect such as temperature or ultraviolet radiation, abbreviated as UV. The modifying component 12 is configured as internal reference source.

Moreover, the sensor 10 comprises an outer housing 13 having an interior 14. A first inlet 15 is integrated into the outer housing 13. Gas can flow from the ambience or environment through the first inlet 15 into the interior 14 of the outer housing 13. Gas can be named air or gaseous matter. Moreover, the sensor 10 comprises an inner housing 16 having an interior 17. The sensing component 11 is arranged in the interior 17 of the inner housing 16. The modifying component 12 is disposed within the interior 14 of the outer housing 13 or is partially disposed within the interior 14 of the outer housing 13 and partially disposed outside of the interior 14 of the outer housing 13.

The first inlet 15 is configured to conduct gas from an outside of the outer housing 13 into the interior 14 of the outer housing 13. The gas is able to diffuse or flow from the interior 14 of the outer housing 13 via the modifying component 12 to the interior 17 of the inner housing 16 and thus to the sensing component 11. Thus, the gas is conducted from the interior 14 of the outer housing 13 into the interior 16 of the inner housing 17 and adjacent to the sensing component 11.

The sensing component 11 generates a sensing component signal SI which corresponds to the ozone concentration of the gaseous matter within the interior 17 of the inner housing 16. The sensing component 11 may also be named ozone component sensor. The sensing component signal SI can also be named ozone sensing component signal. The sensing component 11 may be realized as a UV sensing component or a metal oxide semiconductor sensing component. The sensing component signal SI typically has a base line and a span, wherein a base line and a span error may potentially be observed.

Figure 4A:
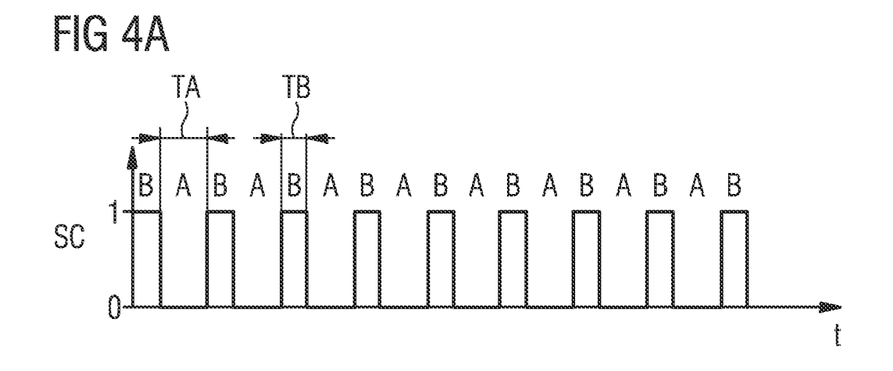
FIGS. 4A to 4D show examples of signals of a sensor.

The modifying component 12 is operable to alter the ozone concentration of the gas within the interior 14 of the outer housing 13 or between the interior 14 of the outer housing 13 and the interior 17 of the inner housing 16. The modifying component 12 is switched off in a first phase A and is switched on in a second phase B (as shown in FIG. 4A). The first and the second phases A, B alternate. The switching on and off of the modifying component 12 leads to a destruction/recovery of the sensing component signal SI.

The sensing component 11 generates the sensing component signal SI as a raw signal SR in the first phase A and as a calibration signal SCA in the second phase B. The ozone concentration in the interior 17 of the inner housing 16 increases in the first phase A and decreases in the second phase B. This effect can be used as in application calibration signal. The calibration signal can be determined in an application that means during operation. Calibration can be performed, since the modifying component 12 produces a physical effect that is predictable. A steady state value of the ozone concentration in the first phase A mainly depends on the ozone concentration in the ambience or environment of the sensor 10. A steady state value of the ozone concentration in the second phase B mainly depends on the modifying component 12 and may be e.g. zero.

In an alternative embodiment, not shown, the modifying component 12 is configured to generate ozone. Thus, the ozone concentration in the interior 17 of the inner housing 16 decreases in the first phase A and increases in the second phase B.

Figure 2:
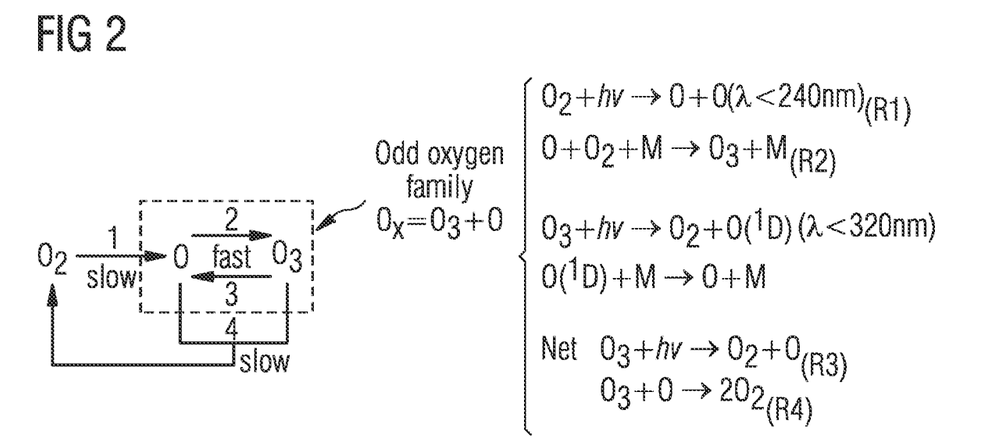
FIG. 2 shows an example of reactions between oxygen and ozone.

FIG. 2 shows an example of reactions between oxygen O2, ozone O3 and molecular oxygen O. An ozone decay can be explained via a Chapman mechanism. A schematic for the Chapman mechanism is shown in FIG. 2. Rate constants for reactions (R1)-(R4) have been measured in the laboratory. Reactions (R2) and (R3) are found to be much faster than reactions (R1) and (R4). There is a rapid cycle between O and O3 by reactions (R2) and (R3), and a slower cycle between O2 and (O+O3) by (R1) and (R4). Because of the rapid cycling between O and O3 it is convenient to refer to the sum of the two as a chemical family, odd oxygen (Ox=O3+O), which is produced by (R1) and consumed by (R4). Simple relationships between O2, O, and O3 concentrations can be derived from a chemical steady-state analysis of the Chapman mechanism.

Figure 3A:
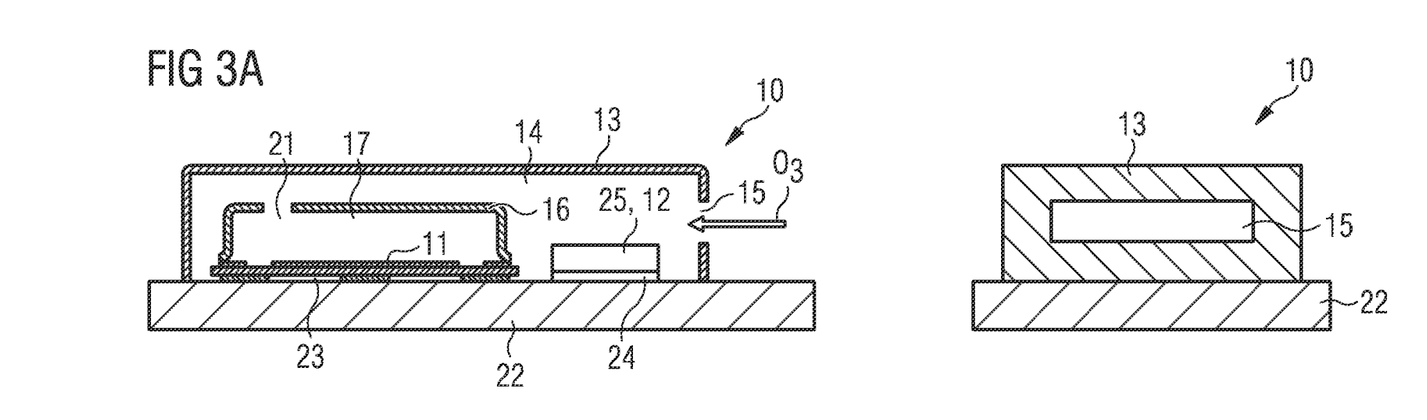
FIGS. 3A to 3E show further examples of a sensor.

FIG. 3A shows an example of the sensor 10 which is a further development of the embodiment shown in FIG. 1. On the left side of FIG. 3A, a cross-section is elucidated. On the right side of FIG. 3A, a view to the first inlet 15 of the outer housing 13 is shown. The inner housing 16 is located inside of the outer housing 13. The inner housing 16 is arranged within the interior 14 of the outer housing 13. The inner housing 16 comprises a second inlet 21. The second inlet 21 is configured to conduct gas from the interior 14 of the outer housing 13 into the interior 17 of the inner housing 16 and adjacent to the sensing component 11. The outer housing 13 can be realized as a lid or overall lid.

The sensor 10 comprises a substrate 22. The sensing component 11 is arranged on the substrate 22. The sensing component 11 may be arranged via a carrier 23 or layer to the substrate 22. The carrier 23 or layer may provide a thermal isolation, for example.

The modifying component 12 is located on the substrate 22. The modifying component 12 may be arranged to the substrate 22 via a body 24 of the sensor 10 or layer of the sensor 10. The body 24 or layer may be designed for thermal isolation of the modifying component 12 to the substrate 22.

The gas, which is also called air or gaseous matter, flows through the first inlet 15 into the interior 14 of the outer housing 13. In the second phase B, the modifying component 12 has an influence on the ozone concentration in the interior 14 of the outer housing 13. The modifying component 12 decreases the ozone concentration in the interior 14 of the outer housing 13. The gas further flows from the interior 14 of the outer housing through the second inlet 21 into the interior 17 of the inner housing 16 and thus to the sensing component 11. Depending on the dimensions and the time constant for diffusion, the ozone concentration decreases in the interior 14 of the outer housing 13 and then the ozone concentration in the interior 17 of the inner housing 16 also decreases.

The first phase A may follow the second phase B. In an embodiment, the sensor 10 is continuously operating. Thus, a first phase A is between two second phases B. A second phase B is between two first phases A.

In the first phase A, the modifying component 12 is switched off. Thus, the ozone concentration inside the interior 14 of the outer housing 13 and consequently also the ozone concentration in the interior 17 of the inner housing 16 and thus at the sensing component 11 rises to the value of the ozone concentration in the ambience or environment. The modifying component 12 has an effect on the gas, for example by the heat generated by the modifying component 12. The modifying component 12 may comprise a heat source 25. The heat source 25 may comprise a resistor. The heat source 25 may be fabricated as a micro-electro-mechanical system, shorted MEMS system. The heat source 25 may be implemented as a micro-heater or hot-plate. The modifying component 12 is configured to increase the temperature of the gaseous matter in the interior 14 of the outer housing 13. The interior 14 of the outer housing 13 can also be named cavity. Therefore, the resistor is able to make the cavity hot. Thus, the modifying component 12 emits infrared radiation.

Advantageously, the inner housing 16 decouples the sensing component 11 from the modifying component 12. The sensor 10 is configured such that the sensor 10 is free of a transfer of radiation from the modifying component 12 to the sensing component 11.

The substrate may be realized as a printed circuit board, abbreviated as PCB, or a ceramic substrate, for example aluminum oxide ceramic or aluminum nitride ceramic. The outer housing 13 is inert with respect to ozone. Alternatively, the interior surface or inner side of the outer housing 13 is covered by a layer which is inert with respect to ozone. Thus, the interior surface of the outer housing 13 has no decreasing or increasing effect on the ozone concentration. For example, the outer housing 13 or a layer at the interior surface of the outer housing 13 is made from a material of a group consisting of an iron-nickel alloy, a noble metal, an epoxide and a polytetrafluoroethylene. For example, the outer housing 13 is realized by a polymer which is coated by a metal layer on the inner side.

Also the inner housing 16 is inert with respect to ozone. The inner housing 16 may be covered at both sides or made from a material of a group consisting of an iron-nickel alloy, a noble metal, an epoxide and a polytetrafluoroethylene.

As shown in FIG. 3A, there is exactly one opening between the interior 14 of the outer housing 13 and the interior 17 of the inner housing 16, namely the second inlet 21. The number of openings between the interior 14 of the outer housing 13 and the interior 17 of the inner housing 16 is exactly one.

The outer housing 13 is attached to the substrate 22. The outer housing 13 may be closed by the substrate 22, wherein the first inlet 15 remains open. The substrate 22 may be named carrier. The attachment of the outer housing 13 to the substrate 22 may be gas-tight or nearly gas-tight. A surface of the substrate 22 is inert with respect to ozone.

The inner housing 16 is also attached to the substrate 22. This attachment may be gas-tight or nearly gas-tight. As shown in FIG. 3A, the inner housing 16 is connected to the carrier 23 that is connected to the substrate 22. Thus, the inner housing 16 is fixed via the carrier 23 to the substrate 22. Alternatively, the inner housing 16 may be directly fixed to the substrate 22.

Advantageously, the inner housing 16 decouples the measuring of the ozone by the sensing component 11 from the destruction of ozone by the modifying component 12.

Alternatively, the sensing component 11 may be directly attached to the substrate 22, e.g. by a glue. The carrier 23 is omitted.

Alternatively, the modifying component 12 may be directly connected to the substrate 22, e.g. by a glue.

In an alternative, not shown, embodiment, the second inlet 21 comprises more than one opening such as two, three, four and more than four openings.

Figure 3B:
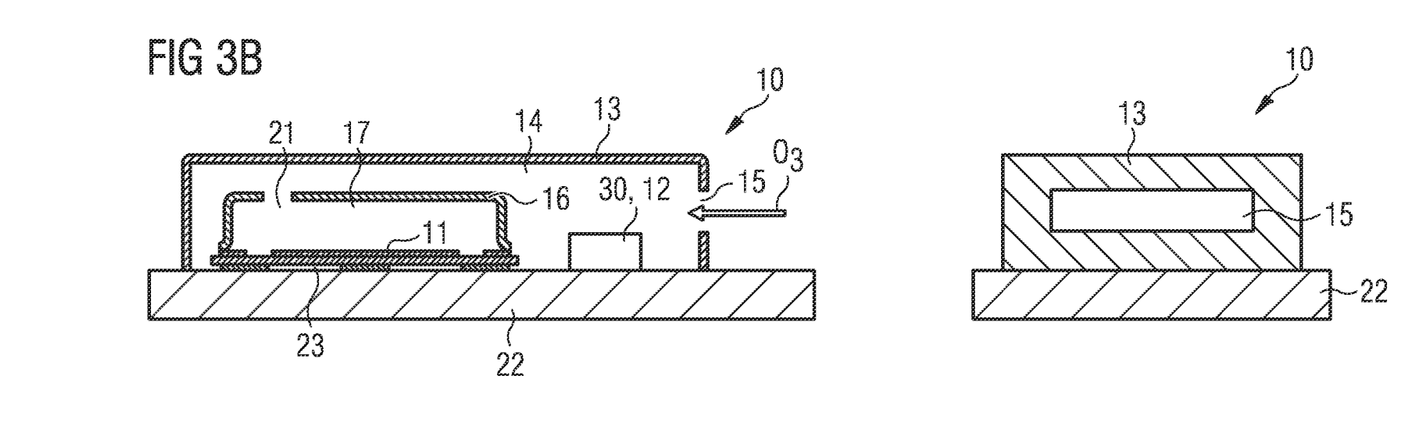

FIG. 3B shows a further example of the sensor 10 which is a further development of the above embodiments. The modifying component 12 comprises a light source 30. The light source 30 may be realized as a light-emitting diode, abbreviated as LED. The LED may be implemented as an ultraviolet radiation LED, abbreviated as UV LED. The modifying component 12 comprises a first number of light sources 30. The first number may be 1, 2, 3, 4 or more than 4. The modifying component 12 has an effect on the gas, namely by the UV radiation emitted by the light source 30. The interior housing 16 and especially the second inlet 21 in the interior housing 16 are located such that any radiation emitted by the light source 30 has only a small influence on the sensing component 11. Advantageously, the modifying component 12 and the sensing component 11 are arranged between the outer housing 13 and the substrate 22.

The sensor 10 may be free of any valve for control of gas-flow or air-flow. The sensor 10 may be free of any pump or fan for movement of gas. Since the sensor 10 is free of any mechanically active part or mechanical actuator, lifetime of the sensor 10 is increased and power consumption is decreased.

The gas inside the interior 17 of the inner housing 16 has only one path to the outside, namely via the second inlet 21, the interior 14 of the outer housing 13 and the first inlet 15. The sensor 10 is free of a further path for the gas that is in the interior 17 of the inner housing 16 to the ambience or environment.

The sensor 10 is not realized as a flow-through system. The sensor 10 is not implemented as a tube system in which gas is able to flow from a first opening of the tube via the modifying component 12 and the sensing component 11 to a second opening of the tube.

Figure 3C:
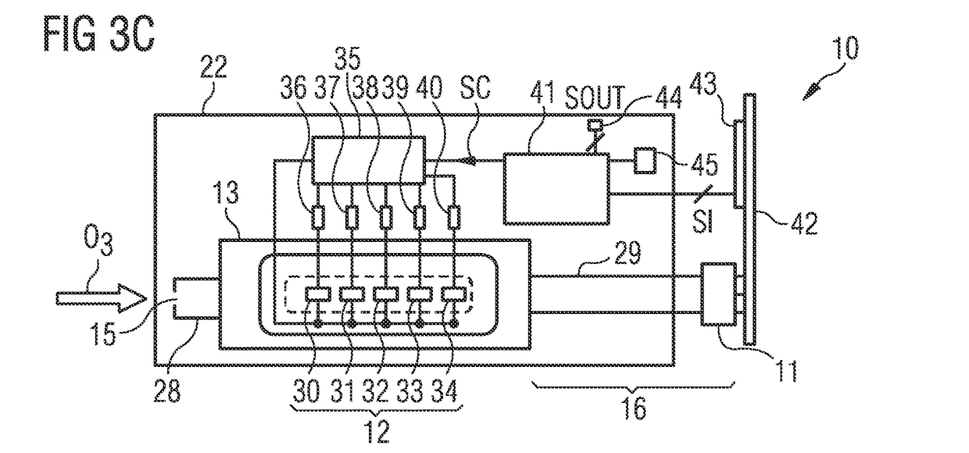

FIG. 3C shows a further example of the sensor 10 which is a further development of the above-shown embodiments. The outer housing 13 is attached to the substrate 22. The outer housing 13 has a first side, not shown, connected to the substrate 22 and a second side which is opposite to the first side. The modifying component 12 is located at the second side. The modifying component 12 comprises at least one light source 30. The light source 30 is realized as a light-emitting diode, abbreviated LED. In the example shown in FIG. 3C, the number of light sources 30 to 34 is five. The sensor 10 comprises a driver 35 that is connected on its output side to the modifying component 12. Thus, the driver 35 is coupled to the terminals of the at least one light source 30. The sensor 10 may comprise a resistor 36 coupling the driver 35 to the at least one light source 30. The at least one light source 30 may be realized as a UV LED. The at least one light source 30 emits light at a wavelength of about 278 nm.

Moreover, the sensor 10 comprises a processor 41 that is connected to the driver 35. The processor 41 may be realized as a microprocessor or a microcontroller. The sensor 10 comprises a memory 45 coupled to the processor 41.

The first inlet 15 is realized as a tube 28. The sensing component 11 is coupled via the inner housing 16 to the outer housing 13. The inner housing 16 may also comprise a tube 29.

The sensor 10 may comprise a further substrate 42 on which the sensing component 11 is attached. A sensor driver 43 of the sensor 10 is arranged on the further substrate 42. The sensor driver 43 is coupled to the sensing component 11. The sensor driver 43 may be coupled to the processor 41. The processor 41 comprises an interface 44 for providing a sensor output signal SOUT.

In an alternative, not shown embodiment, the sensing component 11 and the sensor driver 43 are arranged on the substrate 22. Thus, the further substrate 42 can be omitted.

In an alternative, not shown embodiment, at least two circuits of the processor 41, the sensor driver 43, the memory 45 and the driver 35 are integrated on a semiconductor body.

Figure 3D:
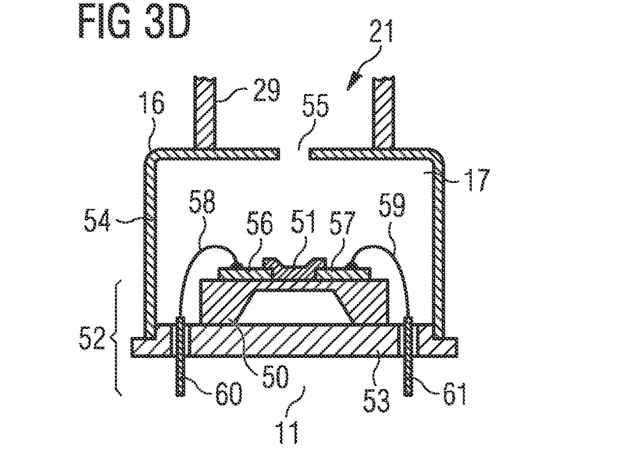

FIG. 3D shows an example of details of the sensor 10 which is a further development of the above-shown embodiments. The sensing component 11 may comprise a hot-plate structure 50 which includes a heater. The sensing component 11 may be fabricated as a micro-electro-mechanical system, shorted MEMS system. The sensing component 11 may be realized as tungsten-oxide or tungsten-trioxide sensing component, shorted WO3 sensing component. The sensing component 11 may be operated in an isothermal manner. The sensing component 11 has a sensing layer 51 on the hot-plate structure 50. The sensing layer 51 may e.g. comprise tungsten-trioxide.

The sensing component 11 may be on a transistor outline package 52, shorted TO package. The TO package 52 comprises a header 53 and a cap 54. The carrier 23 may be realized by the header 53 of the TO package 52. The inner housing 16 may comprise the cap 54 of the TO package. The cap 54 has an opening 55. The second inlet 21 may be realized by the opening 55 of the cap 54 and the tube 29. The tube 29 is fixed to the cap 54. The header 53 and the cap 54 are both metallic. Alternatively, the cap 54 is made out of a polymer. Electrodes 56, 57 of the sensing component 11 are coupled via bonding wires 58, 59 to pins 60, 61 of the header 53. The hot-plate structure 50 and thus the sensing component 11 are disposed in the interior 17 of the inner housing 16.

Figure 3E:
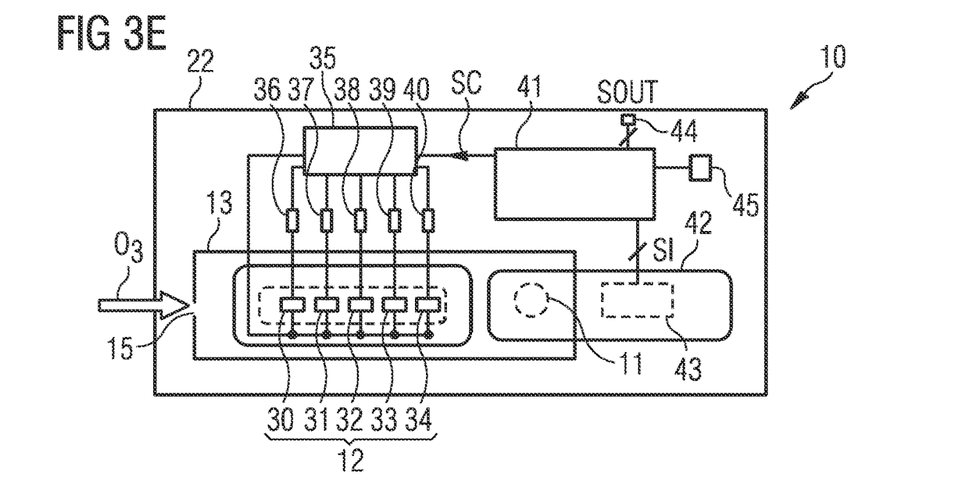

FIG. 3E shows a further example of the sensor 10 which is a further development of the above-shown examples. The tube 29 is omitted. The first inlet 15 is realized as an opening in the outer housing 13. Thus, advantageously, the distance of the ambience to the modifying component 12 is reduced. The inner housing 16 may be realized by the cap 54 of the TO package 52. The cap 54 is directly attached to the outer housing 12. The cap 54 is at least partially located inside the outer housing 13. Thus, the inner housing 16 is disposed within an interior 14 of the outer housing 13. The second inlet 21 is realized by the opening 55 or the openings of the cap 54. Thus, the volume of the inner housing 16 is reduced. The distance of the sensing component 11 to the modifying component 12 is diminished. The sensing component 11 is arranged on the second side of the outer housing 13. The further substrate 42 is attached to the second side of the outer housing 13. Advantageously, the modifying component 12 and the sensing component 11 are accessible from the top of the sensor 10. The modifying component 12 and the sensing component 11 are indirectly disposed on the substrate 22.

The sensing component 11 operates at a constant temperature. The sensing component 11 performs an isothermal operation. The power provided to the sensing component 11 may be for example approximately 40 mW, resulting in a temperature of the sensing component 11 of 300° C.

In an alternative, not shown embodiment, the at least one light source 30 of the modifying component 12 is directly attached to the substrate 22. Thus, the outer housing 13 may be turned by 180 degree with respect to an axis parallel to the substrate 22.

In an alternative, not shown embodiment, the sensing component 11 or the carrier 23 with the sensing component 11 is directly attached to the substrate 22. Thus, the further substrate 42 can be omitted. The carrier 23 may be implemented by the header 53.

FIG. 4A shows an example of a signal of the sensor 10 according to one of the embodiments shown above. A control signal SC is shown as a function of a time t. The control signal SC controls the modifying component 12. In the first phase A, the control signal SC has a first logical value (for example the value 0) and the modifying component 12 is switched off. In the second phase B, the control signal SC has a second logical value (for example the value 1) and thus the modifying component 12 is operating. In the first phase A, the at least one light source 30 does not emit light, whereas in the second phase B the at least one light source 30 emits light. The first phase A and the second phase B alternate. The first phase A and the second phase B are cyclically repeated. The first phase A has a first duration TA and the second phase B has a second duration TB. Alternatively, in the first phase A, the heat source 25 does not provide heat, whereas in the second phase B heat source 25 provides heat.

A cycle consists of one first phase A and one second phase B. A duration of one cycle is equal to TA+TB. The first duration TA may be, for example, between 0.5 seconds and 30 minutes. The second duration TB may be between 0.5 seconds and 60 minutes. Alternatively, the first duration TA may be between 0.5 seconds and 20 minutes and the second duration TB may be between 0.5 seconds and 30 minutes. Alternatively, the first duration TA may be between 0.5 seconds and 20 minutes and the second duration TB may be between 0.5 seconds and 30 minutes. In an example, the first duration TA lasts 10 minutes and the second duration TB lasts 20 minutes. These values are only example values.

Figure 4B:
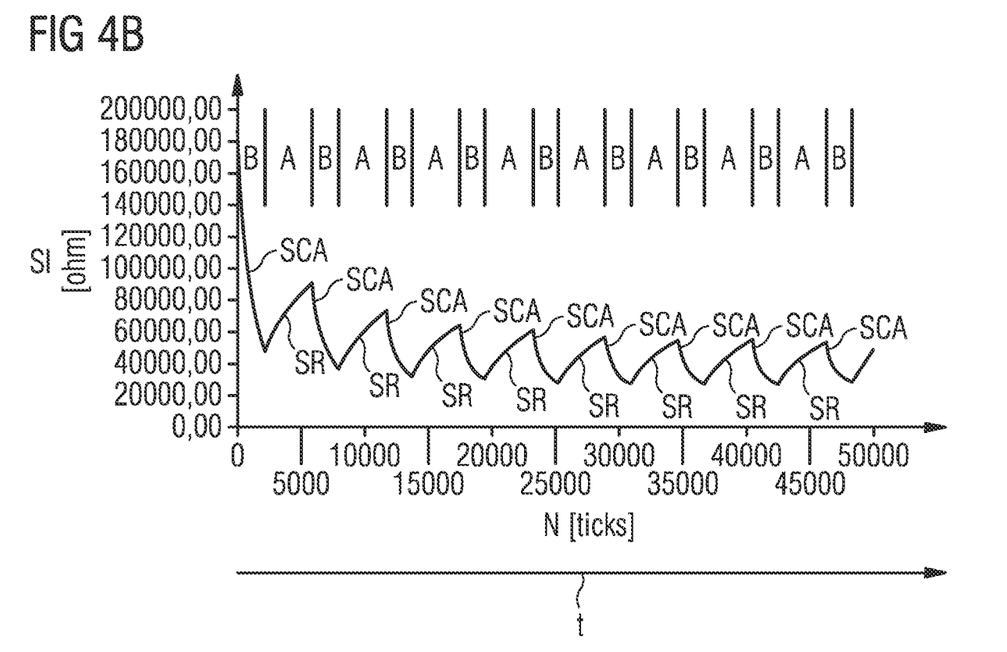

FIG. 4B shows an example of a signal of the sensor 10 according to one of the embodiments shown above. The sensing component signal SI is shown as a function of a number N of ticks which may be the number of measurements. 10000 ticks may be equivalent to about 54 minutes. The sensing component signal SI is shown as a function of the time t. The sensing component signal SI may be e.g. a resistance value of a metal-oxide-semiconductor sensing layer 51 of the sensing component 11. In the example shown in FIG. 4B, the measurement starts with the second phase B. The sensing component signal SI decreases in the second phase B and increases in the first phase A. The sensing component signal SI in the second phase B is named calibration signal SCA and sensing component signal SI in the first phase A is named raw signal SR.

In a cycle, the lowest value of the sensing component signal SI can be achieved at the end of the second phase B and the largest value of the sensing component signal SI can be measured at the end of the first phase A. As shown in FIG. 4B, several cycles are required such that the lowest values of the sensing component signal SI measured in consecutive cycles have approximately the same value and also the highest values of the sensing component signal SI measured in consecutive cycles have approximately the same value. Thus, the system stabilizes after turning on. The ozone concentration may be constant in the measurement shown in FIG. 4B.

Figure 4C:
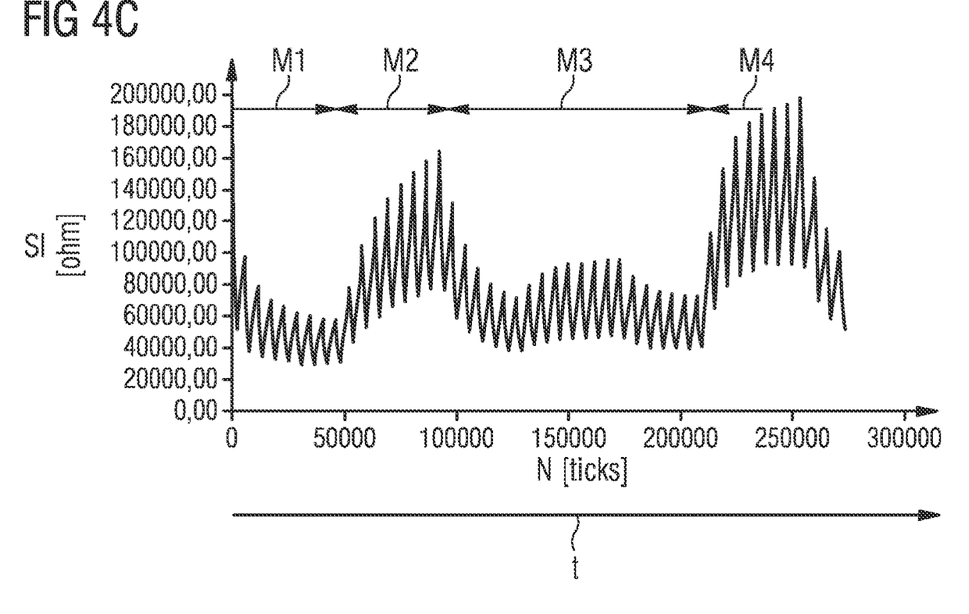

FIG. 4C shows the sensing component signal SI as a function of the number of ticks N. In FIG. 4C, a longer time period in comparison to FIG. 1B is shown. Measurement is performed at different concentrations of ozone. In a first measurement phase M1 an ozone concentration of approximately 0 ppb is supplied to the sensor. In a second measurement phase M2, an ozone concentration of 50 ppb is provided to the sensor 10. In a third measurement phase M3, an ozone concentration of 100 ppb is applied to the sensor 10. In a fourth measurement phase M4, an ozone concentration of 150 ppb is given to the sensor 10. The measurement results can be interpreted as follows: During each of the second phases B, the modifying component 12 is on (that means active) and thus the ultraviolet light emitted by the at least one light source 30 is present. Thus, the sensing component signal SI which is the resistance of the metal oxide semiconductor resistor falls. Thus, it can be assumed as a hypothesis that in the second phase or phases B, the ozone destruction occurs in the outer housing 13. If the fall of the resistance value stops, a zero ozone concentration is reached. This would result in a reset of a baseline. At low values of the ozone concentration, the baseline BL can be correct.

In the first phase A, the modifying component 12 is idle, thus there is no ultraviolet light emitted by the at least one light source 30. Therefore, the sensing component signal SI increases. As a hypothesis it can be assumed that the ozone concentration is not destroyed in the first phase or phases A. Assuming a fixed destruction rate (or generation rate) that is proportional to, for example, the ultraviolet intensity, this procedure can be used to calibrate the sensor sensitivity (that means a span reset).

The sensor output signal SOUT may be a function of the difference between the largest and the lowest value of the sensing component signal SI in a cycle. Thus, the sensor output signal SOUT may be a function of the difference between the value of the sensing component signal SI at the end of the first phase A and the value of the sensing component signal SI at the end of the second phase B. Thus, the sensor output signal SOUT may be a function of the difference between the highest value of the raw signal SR and the lowest value of the calibration signal SCA.

Alternatively, the sensor output signal SOUT is a function of the differences of a first number N of cycles, such as an average of the differences of the first number N of cycles. N may be 1, 2, 3, 4 or more than 4.

In an alternative embodiment, not shown, the modifying component 12 is realized as an ozone source. Thus, the sensing component signal SI (being the raw signal SR)

decreases in the first phase or phases A and the SI (being the calibration signal SCA) increases in the second phase or phases B.

Figure 4D:
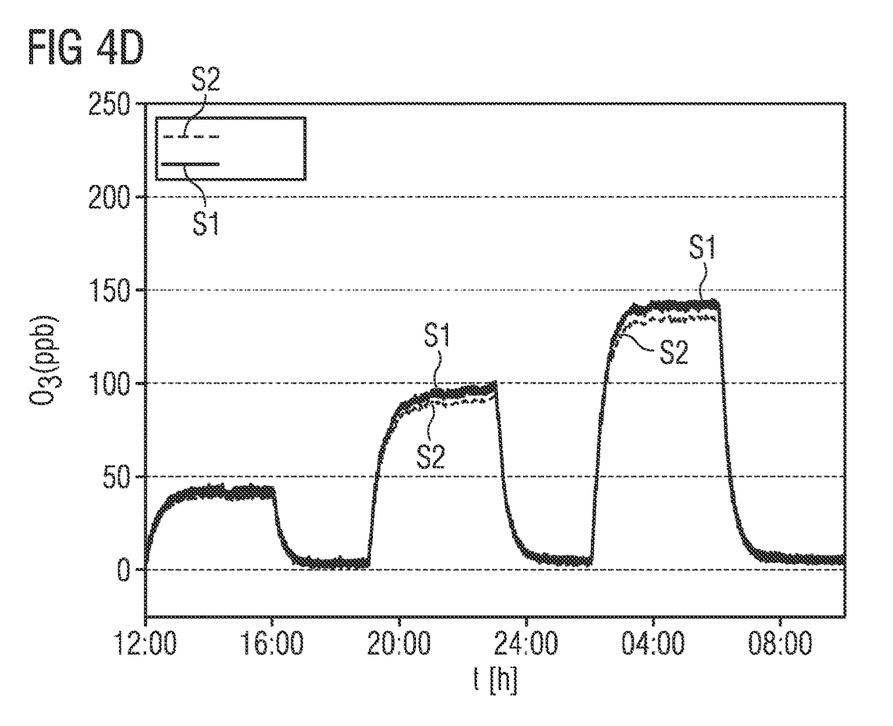

FIG. 4D shows an example of signals of analyzers. The signals are shown as a function of the time t. A first and a second signal S1 are determined by commercial ozone analyzers. The timing schedule of the ozone concentrations for generating these signals S1, S2 correlate with the timing schedule used for the measurement shown in FIG. 4C. Approximately, the following ozone concentrations are applied to the analyzers: 50 ppb, 0.0 ppb, 100 ppb, 0 ppb, 150 ppb, 0 ppb.

Figure 5A:
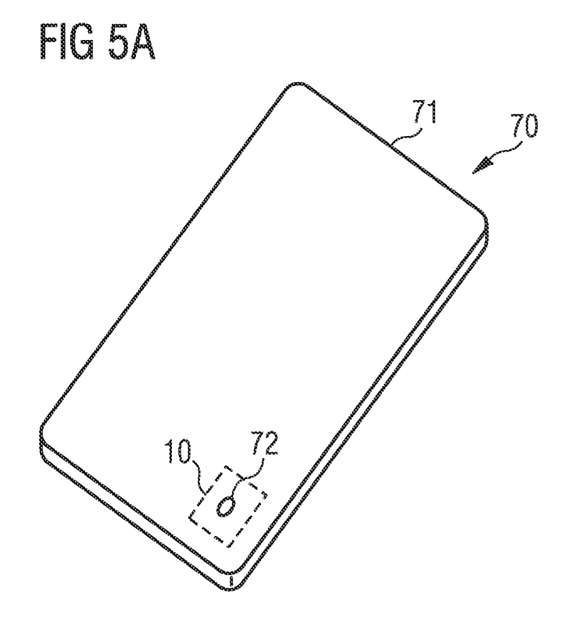
FIGS. 5A to 5C show examples of an apparatus with a sensor.

FIG. 5A shows an example of an apparatus 70 with a sensor 10 that is realized as shown above. The apparatus 70 is realized as a mobile device 71. The sensor 10 is incorporated inside the mobile device 71. A cover of the mobile device 71 has an opening 72 for entry of air to the sensor 10. The mobile device 71 may be a device for mobile communication, a smart device, a smart speaker or a home automation device.

Figure 5B:
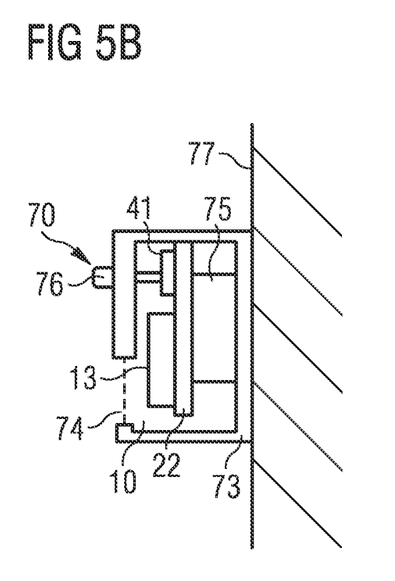

FIG. 5B shows an example of the apparatus 70 with a sensor 10 that is realized as shown above. The apparatus 70 is realized as an indoor air monitor. The apparatus 70 has a housing 73 holding the sensor 10. The housing 73 comprises an opening 74 (optionally with a sieve) to allow penetration of the gas to be detected to the sensor 10. The apparatus 70 may comprise e.g. a battery 75 connected to the sensor 10 for power supply. An indicator 76 may be connected to the sensor 10. The indicator 76 is implemented e.g. as a buzzer and/or a light source that provides an alarm when the sensor 10 measures an ozone concentration above a predetermined threshold. The apparatus 70 may be fixed to a wall 77.

Alternatively, the apparatus 70 is realized as an outdoor air monitor, an automotive air monitor and an industrial air or gas monitor and a device for control of an ozone disinfection apparatus. The apparatus 70 may be portable or fixed to a carrier such as the wall 77, a ceiling, a machine etc.

Alternatively, the apparatus 70 may be connected to a mobile device such as a device for mobile communication, a smart device, a smart speaker or a home automation device by a cable or wireless. The apparatus 70 may provide the measurement result to the mobile device and/or receive the electric power from the mobile device.

Figure 5C:
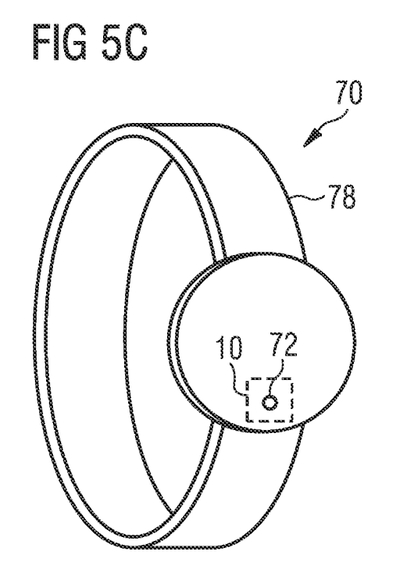

FIG. 5C shows an example of the apparatus 70 with a sensor 10 that is realized as shown above. The apparatus 70 is realized as a wearable device 78. The sensor 10 is incorporated inside the wearable device 78. A housing or cover of the wearable device 78 has the opening 72 for entry of air to the sensor 10. The wearable device 78 may be a watch, a smart ring or an electronic textile.

The embodiments shown in the FIGS. 1 to 5C as stated represent exemplary embodiments of the improved sensor, therefore they do not constitute a complete list of all embodiments according to the improved sensor. Actual sensor configurations may vary from the embodiments shown in terms of shape, size and materials, for example.

The invention claimed is:

1. A sensor comprising:
an outer housing;
an inner housing disposed within an interior of the outer housing or connected to the interior of the outer housing;
an ozone sensing component disposed within an interior of the inner housing;
an ozone modifying component disposed within the interior of the outer housing;
a substrate on which the ozone sensing component and the ozone modifying component are disposed;
a first inlet integrated into the outer housing, the first inlet being configured to conduct ambient gaseous matter from an outside of the outer housing into the interior of the outer housing; and
a second inlet integrated into the inner housing, the second inlet being configured to conduct the gaseous matter from the interior of the outer housing into the interior of the inner housing and adjacent to the ozone sensing component,
wherein the ozone sensing component is configured to generate a sensing component signal corresponding to an ozone concentration of the gaseous matter within the interior of the inner housing,
wherein the ozone modifying component is configured to alter the ozone concentration of the gaseous matter within the interior of the outer housing,
wherein the ozone modifying component includes a light source,
wherein the light source is configured to generate light comprising one or more wavelengths suitable for a photo-decomposition of ozone,
wherein the ozone modifying component is configured to decrease the ozone concentration of the gaseous matter within the interior of the outer housing,
wherein an interior surface of the outer housing is substantially reflective to the one or more wavelengths,
wherein the interior surface of the outer housing is covered or made from a material comprising an iron-nickel alloy, a noble metal, an epoxide or a polytetrafluoroethylene,
wherein the sensor is configured so that the ambient gaseous matter flows or diffuses from an ambience via the first inlet, the interior of the outer housing, the second inlet and the interior of the inner housing to the ozone sensing component,
wherein the inner housing and the ozone modifying component are arranged laterally side by side on the substrate, and
wherein the outer housing laterally surrounds the inner housing and the ozone modifying component.

2. The sensor of claim 1, wherein the ozone sensing component comprises a metal oxide sensor element.

3. The sensor of claim 2, wherein a sensing layer of the metal oxide sensor element comprises one of tungsten oxide or indium oxide.

4. The sensor of claim 1, wherein the ozone modifying component includes a heat source, and wherein the heat source is configured to decrease the ozone concentration of the gaseous matter within the interior of the outer housing.

5. The sensor of claim 1, wherein the ozone modifying component includes a plasma source, and wherein the plasma source is configured to decrease the ozone concentration of the gaseous matter within the interior of the outer housing.

6. The sensor of claim 1, wherein the ozone modifying component includes an ozone source, wherein the ozone source is configured to increase the ozone concentration of the gaseous matter within the interior of the outer housing.

7. The sensor of claim 1, further comprising:
a processor; and
a memory,
wherein the processor is communicatively coupled to the ozone sensing component and the ozone modifying component, and wherein the memory is communicatively coupled to the processor, the processor being configured to:
generate a raw signal with the ozone sensing component;
record the raw signal at the memory;
activate the ozone modifying component;
generate a calibration signal with the ozone sensing component;
record the calibration signal at the memory; and
deactivate the ozone modifying component.

8. The sensor of claim 1, wherein the sensor is free of a pump, a ventilator and a valve.

9. An apparatus comprising:
the sensor of claim 1,
wherein the apparatus is realized as one of the group consisting of a wearable device, a mobile device, an indoor air monitor, an outdoor air monitor, an automotive air monitor, an industrial air or gas monitor, and a device for controlling an ozone disinfection apparatus.

10. A method for using the sensor of claim 1, the method comprising:
generating a raw signal with the ozone sensing component;
activating the ozone modifying component;
generating a calibration signal with the ozone sensing component; and
deactivating the ozone modifying component.

11. The method of claim 10, further comprising determining the ozone concentration of the gaseous matter outside of the outer housing from a plurality of raw signals and a plurality of calibration signals.

12. A method for using a sensor comprising an outer housing, an inner housing disposed within an interior of the outer housing or connected to the interior of the outer housing, an ozone sensing component disposed within an interior of the inner housing, an ozone modifying component disposed within the interior of the outer housing, a substrate on which the ozone sensing component and the ozone modifying component are disposed, a first inlet integrated into the outer housing and a second inlet integrated into the inner housing, wherein the ozone modifying component includes a light source, wherein the light source is configured to generate light comprising one or more wavelengths suitable for a photo-decomposition of ozone, wherein the ozone modifying component is configured to decrease an ozone concentration of a gaseous matter within the interior of the outer housing, wherein an interior surface of the outer housing is substantially reflective to the one or more wavelengths, and wherein the interior surface of the outer housing is covered or made from a material comprising an iron-nickel alloy, a noble metal, an epoxide or a polytetrafluoroethylene, the method comprising:
generating, by the ozone sensing component, a raw signal;
activating the ozone modifying component;
generating, by the ozone sensing component, a calibration signal; and
deactivating the ozone modifying component,
wherein an ambient gaseous matter flows or diffuses from an ambience via the first inlet, the interior of the outer housing, the second inlet and the interior of the inner housing to the ozone sensing component,
wherein the inner housing and the ozone modifying component are arranged laterally side by side on the substrate, and
wherein the outer housing laterally surrounds the inner housing and the ozone modifying component.

13. The method of claim 12, further comprising determining the ozone concentration of the ambient gaseous matter from a plurality of raw signals and a plurality of calibration signals.

* * * * *